(12) United States Patent
Pednekar et al.

(10) Patent No.: US 10,302,732 B2
(45) Date of Patent: May 28, 2019

(54) REAL-TIME ADAPTIVE PHYSIOLOGY SYNCHRONIZATION AND GATING FOR STEADY STATE MR SEQUENCES

(71) Applicant: KONINKLIJKE PHILIPS N.V., Eindhoven (NL)

(72) Inventors: Amol Pednekar, Eindhoven (NL); Raja Muthupillai, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 345 days.

(21) Appl. No.: 15/038,772

(22) PCT Filed: Nov. 21, 2014

(86) PCT No.: PCT/EP2014/075285
§ 371 (c)(1),
(2) Date: May 24, 2016

(87) PCT Pub. No.: WO2015/082234
PCT Pub. Date: Jun. 11, 2015

(65) Prior Publication Data
US 2016/0377693 A1  Dec. 29, 2016

Related U.S. Application Data

(60) Provisional application No. 61/910,526, filed on Dec. 2, 2013.

(30) Foreign Application Priority Data

Jan. 16, 2014 (EP) ..................................... 14151372

(51) Int. Cl.
*G01R 33/54* (2006.01)
*G01R 33/567* (2006.01)
(Continued)

(52) U.S. Cl.
CPC ........ *G01R 33/5673* (2013.01); *A61B 5/0205* (2013.01); *G01R 33/34* (2013.01);
(Continued)

(58) Field of Classification Search
CPC .............. G01R 33/546; G01R 33/5614; G01R 33/5676
(Continued)

(56) References Cited

U.S. PATENT DOCUMENTS 5,051,903 A   9/1991 Pelc
5,251,629 A  10/1993 Koizumi et al.
(Continued)

OTHER PUBLICATIONS

Oppelt et al "FISP: Eine Neue Schnelle Pulssequenz Fuer Die Kernspintomographie . . . " Electromedia vol. 54, No. 1, Jan. 1, 1986.
(Continued)

*Primary Examiner* — Patrick Assouad
*Assistant Examiner* — Demetrius R Pretlow

(57) ABSTRACT

The present invention is related to a method of acquiring free-breathing steady-state magnetic resonance images (MRI) and a free-breathing Magnetic Resonance (MR) imaging system (10) for generating a MR image of a test subject (20) at least comprising a magnetic field unit, a control unit for controlling functions of the MR imaging system, an image processing unit and a user interface capable of receiving parameters defining a MR-pulse sequence, wherein the MR imaging system further comprises a detection unit (36) for detecting physiological activity of a test subject and a data processing unit (40) capable of performing statistical analysis of the physiological activity data and capable to adaptively tailor at least one of the parameters of the MR-pulse sequence based on the statistical analysis. This includes at least adjustment of at
(Continued)

least the starting points and/or the duration of dummy excitations which are part of the MR-pulse sequence.

20 Claims, 3 Drawing Sheets

(51) Int. Cl.
 G01R 33/561 (2006.01)
 A61B 5/0205 (2006.01)
 G01R 33/34 (2006.01)
 G01R 33/385 (2006.01)
 A61B 5/055 (2006.01)
 A61B 5/08 (2006.01)
(52) U.S. Cl.
 CPC ......... *G01R 33/385* (2013.01); *G01R 33/546* (2013.01); *G01R 33/5614* (2013.01); *G01R 33/5676* (2013.01); *A61B 5/055* (2013.01); *A61B 5/08* (2013.01)
(58) Field of Classification Search
 USPC ........................................................ 324/322
 See application file for complete search history.

(56) References Cited

U.S. PATENT DOCUMENTS

| | | | |
|---|---|---|---|
| 5,363,844 A | 11/1994 | Riederer | |
| 6,438,404 B1* | 8/2002 | Van Den Brink | ........................... G01R 33/56308 324/306 |
| 7,047,060 B1* | 5/2006 | Wu | ....................... G01R 33/563 324/307 |
| 7,756,565 B2 | 7/2010 | Salla | |
| 8,137,282 B2 | 3/2012 | Salla et al. | |
| 2002/0149365 A1* | 10/2002 | Demeester | ........... G01R 33/583 324/307 |
| 2004/0155653 A1 | 8/2004 | Larson et al. | |
| 2006/0224062 A1* | 10/2006 | Aggarwal | .......... G01R 33/5673 600/413 |
| 2007/0001674 A1* | 1/2007 | Purdy | ................ G01R 33/5676 324/309 |
| 2008/0129298 A1* | 6/2008 | Vaughan | ............ G01R 33/5612 324/322 |
| 2008/0154121 A1* | 6/2008 | Kouwenhoven | ... G01R 33/5673 600/413 |
| 2008/0161678 A1* | 7/2008 | Miyazaki | ............. A61B 5/0263 600/419 |
| 2008/0309333 A1 | 12/2008 | Stehning | |
| 2009/0018433 A1* | 1/2009 | Kassai | .................... A61B 5/055 600/413 |
| 2009/0245607 A1* | 10/2009 | Sugiura | ................ A61B 5/0263 382/131 |
| 2010/0109665 A1* | 5/2010 | Nielsen | .............. G01R 33/3802 324/309 |
| 2010/0145182 A1* | 6/2010 | Schmidt | .................. G06F 19/00 600/410 |
| 2010/0219830 A1* | 9/2010 | Takei | ................. G01R 33/5635 324/309 |
| 2011/0152669 A1 | 6/2011 | Kassai | |
| 2011/0175609 A1* | 7/2011 | Hu | ..................... G01R 33/3415 324/309 |
| 2011/0210732 A1* | 9/2011 | Worters | ............. G01R 33/5614 324/309 |
| 2012/0230563 A1* | 9/2012 | Vik | ........................ A61B 6/032 382/128 |
| 2012/0268124 A1* | 10/2012 | Herbst | ............. G01R 33/56509 324/309 |
| 2013/0278263 A1* | 10/2013 | Huang | ............... G01R 33/5611 324/309 |
| 2013/0338930 A1 | 12/2013 | Senegas et al. | |
| 2014/0079304 A1* | 3/2014 | Foo | ....................... G06T 11/008 382/131 |
| 2015/0091563 A1* | 4/2015 | Lu | .......................... A61B 5/055 324/309 |
| 2015/0177350 A1* | 6/2015 | Warntjes | ................ G01R 33/50 324/309 |
| 2015/0257660 A1* | 9/2015 | Miyazaki | .............. A61B 5/055 600/413 |
| 2016/0074674 A1* | 3/2016 | Kohli | ................... A61B 5/0205 600/484 |

OTHER PUBLICATIONS

Spuentrup et al "Navigator-Gated Free-Breathing Three-Dimensional Balanced Fast Field Echo. . ." Investigative Radiology vol. 37, No. 11 Jan. 1, 2002 p. 637-642.

Fernandez et al "Adaptive Trigger Delay Using a Predictive Model Applied to Black Blood Fast Spin Echo Cardiac Imaging in Systole" Proceedings of the International Society for Magnetic Resonance in Medicine, Apr. 18-24, 2009, p. 4719.

Vasanawala et al "Fluctuating Equilibrium MRI" Magnetic Resonance in Medicine vol. 42, p. 876-883 (1999).

\* cited by examiner

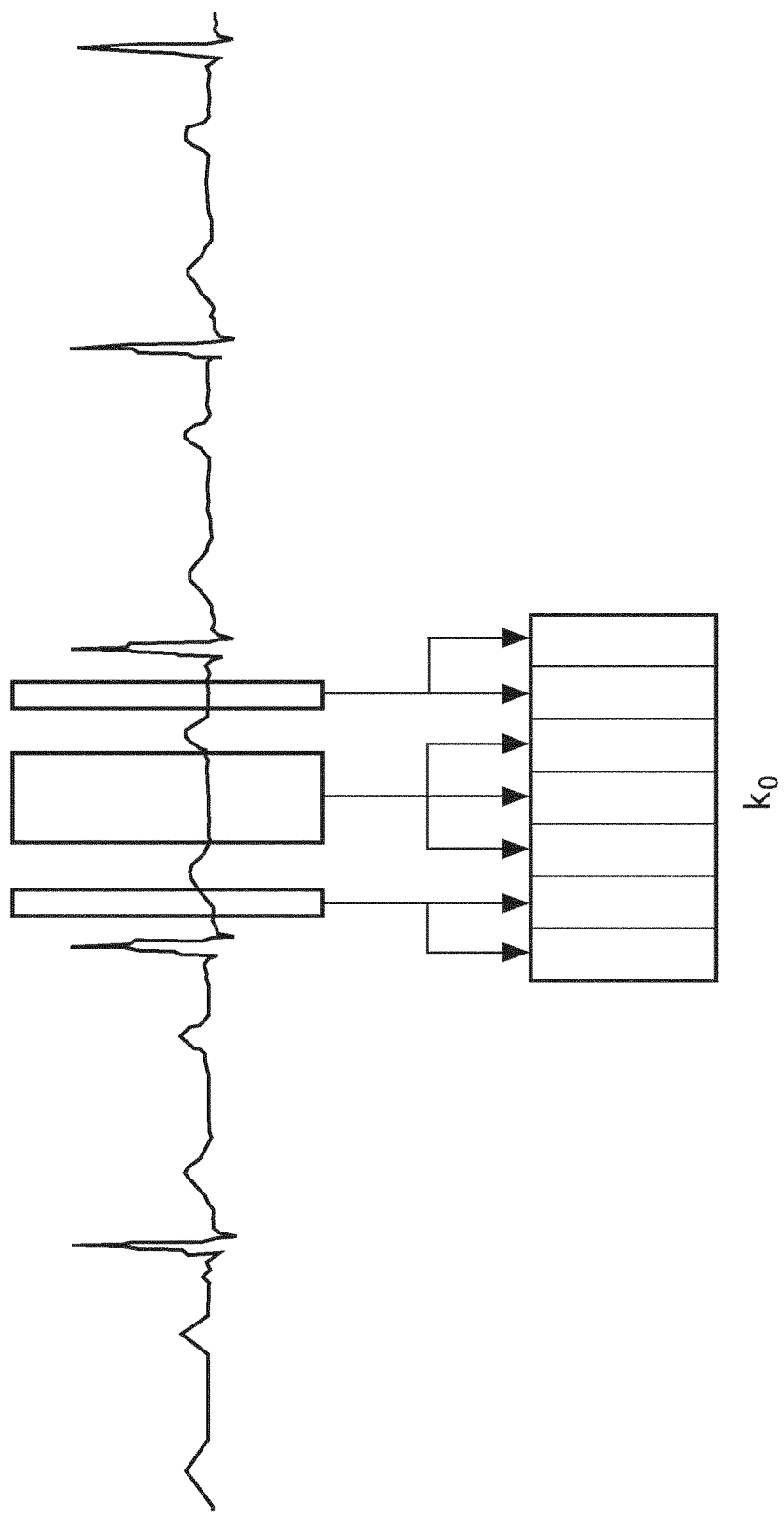

REAL-TIME ADAPTIVE PHYSIOLOGY SYNCHRONIZATION AND GATING FOR STEADY STATE MR SEQUENCES

CROSS REFERENCE TO RELATED APPLICATIONS

This application is a U.S. national phase application of International Application No. PCT/EP2014/075285, filed on Nov. 21, 2014, which claims the benefit of U.S. provisional Application Ser. No. 61/910,526 filed on Dec. 2, 2013 and EP application Serial No. 14151372.1 filed on Jan. 16, 2014, both of which are incorporated herein by reference.

FIELD OF THE INVENTION

The invention pertains to a method of acquiring free-breathing steady-state magnetic resonance images (MRI) and a free-breathing Magnetic Resonance (MR) imaging system for generating a MR image of a test subject at least comprising a control unit for controlling functions of the MR imaging system and a user interface capable of receiving parameters defining a MR-pulse sequence, wherein the MR imaging system further comprises a detection unit for detecting physiological activity of a test subject and a data processing unit capable of performing statistical analysis of the physiological activity data and capable to adaptively tailor at least one of the parameters of the MR-pulse sequence based on the statistical analysis.

BACKGROUND OF THE INVENTION

In the last decades magnetic resonance imaging (MRI) has proven to be a very valuable tool, inter alia in the field of medicinal diagnostics. This is especially true considering the unique features of this technique to gain a better understanding of the human body due to the possibility to obtain real-life 2- or 3-dimensional structural and functional information without the necessity to destroy or damage the tissue of interest. Inasmuch as, the technical parts has been subject to tremendous improvements, e.g. by implementation of higher magnetic field strength or more sophisticated pulse sequences, an image resolution in time and space has been achieved, which deemed impossible just a few years ago. Nevertheless, also today several sources of image artifacts are known, which might possibly limit the achievable image quality. On the one hand image artifacts may be caused by the machine setup and may include main field inhomogeneity, gradient non-linearities, timing errors and RF-interference. On the other hand several reasons for a limited image quality can be directly attributed to motions of the test subject. Here especially respiration, cardiac pulsation, blood and CSF flow, peristalsis, swallowing and voluntary motion of the subject has to be mentioned. Such test subject motions are detrimental, because typically the time scale of MRI data acquisition necessary to make an image (order of seconds) can span a temporal extent that is roughly of the order of or exceeding the time scale at which motion occurs.

One way to overcome such motion artifacts is the introduction of specific boundary conditions on the image data acquisition. The respiratory motion for instance can be countered by data acquisition during suspended breath hold. However, the clinical need for spatial resolution, spatial coverage, and temporal resolution usually puts the total acquisition time beyond the breath holding capacity of the test subjects or patients. This poses the need to reduce the resulting motion artifacts in MRI by either synchronizing the MR imaging with the physiologic signal or by acquiring MR data rapidly enough to freeze the motion.

MR imaging may be synchronized to physiologic signals either by prospective or retrospective gating. In prospective gating, the detection of a specific phase in the physiologic cycle initiates RF excitations and initiates data acquisition for a pre-defined duration. The RF excitation and data acquisition resume only after the next occurrence of the specified physiologic phase. In contrast, in retrospective gating, RF excitation and data acquisition are repeated at a fixed rate with data acquired during a user-identified physiologic phase. The recorded timing of each data acquisition in the physiologic cycle is used to compute a synthetic set of data and images are interpolated to fixed physiologic phases.

One method for accounting of the motion of a subject is disclosed in U.S. Pat. No. 5,251,629. Here a method of and an apparatus for inspecting a physical portion having physiological movement, for example, the abdominal region moving with breathing, by utilizing nuclear magnetic resonance is described. The circumstances of that area of the surface of the abdominal region which exists on a plane indicative of a slice to be imaged, is made different from the circumstances of the surface of the remaining physical portion. In this case, a person to be inspected feels a foreign matter at the abdominal region, and suppresses the movement of the abdominal region due to breathing, consciously and unconsciously, thereby moving the breast with breathing. Thus, the to-be-inspected abdominal region is kept quiet, and an accurate inspection can be made in a short period of time.

Further, US 2008/0154121 A1 describes a magnetic resonance imaging method that involves detection of a series of trigger events and acquisition of successive segments of magnetic resonance signals from respective segments of k-space. The occurrence of the next trigger event is predicted, e.g. by way of a running average, on the basis of the detected series of trigger events. Acquisition of at least one individual segment of magnetic resonance signals is triggered on the basis of the occurrence of the predicted trigger event. Triggering of the acquisition is based on the predicted trigger event, e.g. in that the instant and duration of the acquisition is adjusted on the basis of the prediction of the trigger event.

According to US 2011/0152669 A1, a magnetic resonance imaging apparatus is provided which performs myocardial perfusion imaging of an object. The apparatus comprises an imaging unit which acquires image data by imaging a heart of the object in synchronism with a biological signal from the object, and an image generating unit which generates an image concerning the heart of the object based on the image data, wherein the imaging unit applies a probe pulse for detecting body motion of the object before imaging of the heart, and applies a spatial nonselective saturation pulse before application of the probe pulse, and a local selective pulse for flipping back a flip angle of the spatial nonselective saturation pulse with regard to a region to which the probe pulse is applied.

US 2008/0309333 A1 describes a magnetic resonance system for acquiring MR data from a subject, the MR system comprising a monitoring module for monitoring a characteristic of a motion of the subject, the characteristic of the motion having a pre-determined or dynamically adjusted limit, and a pulse sequencer for applying a pulse sequence to acquire data from the subject when the characteristic of the motion is within the limit, the pulse sequence comprising at least one pulse waveform, wherein the pulse sequencer is further arranged to regulate a characteristic of the at least one pulse waveform when the characteristic of the motion surpasses the limit.

In U.S. Pat. No. 5,051,903 an apparatus for reducing image artifacts in NMR imaging is described. The apparatus matches elements of a set to values of a substantially periodic function so that the values exhibit a predetermined relationship to the elements. The matching is performed by evaluating the relative probability of the values of the substantially periodic function from the samples in the growing database of the values and assigning the values to the elements by using the evaluated relative probability, so as to maximize the probability that subsequent valves may be assigned the remaining elements according the predetermined relationship.

In "Fernandez B. et al: Adaptive trigger delay using a predictive model applied to black blood fast spin echo cardiac imaging in systole", Proceedings of the International Society for Magnetic Resonance in Medicine, ISMRM, 17th Scientific Meeting and Exhibition, Honolulu, Hi., USA, 18-24 Apr. 2009, page 4719" it is described to acquire black blood fast spin echo in end-systolic phase by launching the double inversion recovery before the R-wave in the previous cardiac cycle.

Nevertheless, besides the above mentioned way to care about motions in MRI special requirements have to be fulfilled in specific steady state MR sequences, which are very important in the context of cine cardiac MR (CMR). One preferred sequence for cine CMR the balanced steady-state free precession (bSSFP) sequence, which is widely used for evaluating global (end-diastolic volume, end-systolic volume, and ejection fraction) and regional (wall motion, wall thickening) ventricular functions due to its superior blood-to-muscle contrast and higher intrinsic signal to noise (SNR) ratio.

The conventional bSSFP acquisition applies a pre-defined set of RF excitations during which data acquisition is disabled (dummy excitations). These dummy excitations drive the magnetization toward steady state, after which data acquisition commences. Once the steady state is reached, any interruption in the periodic application of RF pulses will drive the magnetization away from steady state and resumption of RF excitations will introduce transient signal oscillations. To avoid this, all data required for image formation is acquired immediately without any interruption by regular application of RF pulses, once the steady state is established.

SUMMARY OF THE INVENTION

There is a need for a further improved system that is able to diminish the burden of the breath-holding constraint in steady state MR sequences such as bSSFP, and allowing these sequences to be used with irregularly spaced interruptions in synchronization with physiologic signals in a free-breathing experiment.

In this context, the steady state constraint places significant burden on data acquisition with periodic interruptions stemming from the desire to time the data acquisition to a pre-defined respiratory phase or over a number of cardiac cycles beyond the ability of patients to suspend respiration via breath-holding. Constant application of dummy RF pulses to avoid the interruption of steady state also imposes a specific absorption rate (SAR) burden and is not a viable method for relatively long acquisitions.

It is therefore an object of the invention to provide an improved Magnetic Resonance (MR) imaging system for generating a MR image of a test subject.

According to the invention, this object is addressed by a Magnetic Resonance (MR) imaging system for generating an MR image of a test subject, the MR imaging system at least comprising:
    a control unit for controlling functions of the MR imaging system,
    a user interface capable of receiving parameters defining a MR-pulse sequence,
    a detection unit for detecting physiological activity of the test subject and
    a data processing unit capable of performing statistical analysis of the physiological activity data and capable to adaptively tailor at least one of the parameters of the MR-pulse sequence based on the statistical analysis, including adjustment of at least the starting points and/or the duration of RF-dummy excitations which are part of the MR-pulse sequence.

Due to the inventive combination of a detection unit in combination with a data processing unit it is possible to tailor the MR pulse sequence for future scans on the basis of a statistical analysis. The statistical analysis of physiological cycles provides the input for instance for triggering data acquisitions in periods, where motions of the test subjects are unlikely. Therefore, it is unnecessary to request breath-holding from the test subject. In addition, in contrast to the standard methods of retrospective gating such system is able to provide the requirements to actively tailor the pulse sequence in real-time. Such system is able not only to track the physiological activity of a test subject and use the information afterwards for combination of different scans to form an image. Such system is able to actively influence the acquisition parameter for further scans of the same sequence. Therefore, the likelihood of artifacts, caused by the physiological activity of the test subjects is reduced, resulting in the acquisition of better MR images.

Surprisingly it has been found that the inventive system is capable of providing a solution for several applications which cannot be assessed with state of the art breath-holding systems. The inventive system can for instance be used in pediatric applications, wherein sedated kids cannot perform breath-hold. The current breath-hold solution has to average over multiple acquisitions, which in turn suffer from motion blurring, long scan duration, and high SAR. Hence, standard breath-hold images are typically obtained with poorer spatial and temporal resolution than adequate for smaller structures and rapid heart rates in pediatric population. The proposed magnetic resonance system is able to deliver artifact free images with no compromise in terms of SNR, CNR, edge definition, SAR, and scan duration during free breathing of the subject. Such finding is also true in all cases where the test subjects suffer from a compromised breath holding capacity.

Furthermore, it has been found that above free breathing system is able to allow a higher temporal resolution up to 6-12 msec with the same spatial resolution which enables assessment of transient phenomena like peak ejection rate, peak filling rate, active filling rate, and even iso-volumetric relaxation time. In routine clinical practice usually temporal resolution is limited to 30-50 msec to keep breath-hold at 8-12 R-R intervals.

In addition, the free-breathing system is especially useful in the case of 3D cine imaging. 3D multi-phase iso-volumetric acquisition with or without contrast administration has potential to make 2D acquisitions in multiple orientations redundant as one can perform multi-planar reconstruction in desired orientations. Conventional breath hold cine acquisition does not permit adequate spatial resolution for 3D acquisition. In addition, single shot 3D saturates the blood signal in entire LV thus significantly reducing the fresh blood signal. The proposed free breathing system in conjunction with parallel imaging can allow iso-volumic 3D cine acquisitions. The interrupted RF excitations of every respiratory cycle also ensure improved bright blood signal compared to conventional 3D cine acquisition. 3D cine is especially useful in pediatric cases, where long-axis dimension is smaller and need for multi-planar reconstruction to evaluate congenital cases is critical.

The inventive system has also several advantages that can be used to acquire proximal coronary artery structure. This data will be useful to study coronary dynamics and related mechanical stress/strain. The cine frames can also be utilized to perform retrospective reconstruction where multiple frames from quiescent periods can be merged to achieve higher SNR.

Besides the above mentioned advantages the inventive system also allows two image acquisitions. Thus, one can utilize for instance non-uniform spectral response of bSSFP to suppress fat from two acquisitions with different RF phase cycling schemes [see also MRM 42:876-883, 1999]. This may be useful in the evaluation of fatty infiltration along with the motion in cases like arrhythmogeneic right ventricular dysplasia.

The inventive MR imaging system can advantageously be based on the imaging hardware of existing MR-systems, which are commercially available on the market. Such systems can provide all standard elements of the MR, like the magnet, RF-coils, receiver, scanner console, computer etc. and can additionally be equipped or modified according to the requirements of the invention. As far as calculations are required also the standard computer system of a standard MR-system can be used, advantageously by modification of the software package.

Within a MR-pulse sequence all necessary experimental parameters are defined. This parameter usually are a function of the tissue of interest and may include maximum scan time (MST), time to steady state (TSS), time for repetition (TR), time to echo (TE) and flip angle (FA). Usually the parameters are stored in the measurement program file (MPF) which executes on the spectrometer.

A suitable detection unit for detecting the physiological activity of a test subject may include standard detection devices known to the skilled in the art. Such units may for instance include an ECG, a pulse meter, a respiratory trigger and/or a RF-monitor. Test subjects in the sense of the invention may for instance be humans or animals.

A data processing unit capable of performing statistical analysis may for example be a standard computer including a statistical software package. Such computer may be already part of a standard MR system and may be upgraded by a special statistical package. The statistical analysis may include the calculation of averages, moving averages, histogram analysis, maximum-likelihood or maximum-entropy estimation or any other kind of statistical analysis which is able to reduce a given data set to a defined mathematical model including one or more statistical parameter. The parameter may include just the data points of one detection unit or may favorably include the data points of two or more separate detection units in order to include all possible sources of motion artifacts for an image.

According to a preferred embodiment of the invention, the system further comprises a magnetic field unit and an image processing unit.

Another aspect of the invention provides a system, wherein the statistical analysis of the physiological activity data at least comprises determination of the periodicity of the respiratory and/or the cardiac cycle of a test subject. It has been found that the periodicity of the respiratory and/or the cardiac cycle may be an important parameter for adaptively tailoring the MR-sequence. The respiratory and the cardiac cycle are the cause of major movements of a test subject during a free breathing experiment. Therefore, determination of the periodicity of both cycles and adaption of the sequence parameter of future scans based on these periodicities may provide a useful tool for tailoring the data acquisition in periods, wherein no or only minor movements of the test subjects can be expected. Therefore, the likelihood of motion artifacts in the image is reduced.

Furthermore, a system is within the scope of the invention, wherein the MR-pulse sequence is a balanced steady state free precession sequence. Especially in the course of a steady-state MR sequence the inventive system might be able to reduce the likelihood of motion artifacts. In standard prospective gating procedures a MR signal may be prospectively gated to acquire also in conjunction with respiratory signal. Typical is a fast acquisition speed in order to freeze the motion, rapid repeated excitations of gradient echoes are employed with segmented traversal though k-space for minimal exposure to motion and RF flip angle schemes to catalyze approach to stead state. In prospective gating instances, the MR signal acquisition process is interrupted with a trigger whose regularity is governed by a physiologic process such as respiration or cardiac pulsation. In rapid repeated excitation gradient echo MR sequences where a periodic uninterrupted application of RF pulses is necessary to maintain a steady state of the magnetization (known as steady state sequences), these interruptions can result in significant transient oscillating approach back to presumed steady state of the MR signal. Such interruptions within the physiologic synchronization constraint are addressed by the inventive system, which is especially useful if the steady state requirement for an MR sequence has to be fulfilled.

In addition, it is within the scope of the invention to disclose a system, wherein the data processing unit is capable to tailor RF-excitation and/or the start of the data acquisition. Such tailoring may for instance either be performed by change of the measurement program file (MPF) or by modification of the program definition file (PDF) by the data processing unit. The system is able to determine the most suited points in time, wherein data acquisition can be performed with no or only minor influence of the physiological activity. Therefore, it is possible to predict the best time for data acquisition and in the course of a steady state experiment also RF-excitation has to be adapted. Only tailoring of both steps, excitation and acquisition, may ensure the generation of an artifact free image.

An additional inventive aspect provides a system, wherein the data processing unit is capable to tailor the k-space sampling. Based on the physiological activity of the test subject and the statistical analysis provided by the data processing unit it is possible to adaptively adjust (tailor) the number of k-space segments in order to maximize scan efficiency. Due to the known periodicities it is possible to completely fill the remaining time available with data acquisition for the current physiologic cycle. In addition, it is possible to adjust the k-space sampling in a way that will minimize the likelihood of motion during the information-rich, central-portions of k-space. This may be achieved by e.g. prospectively planning to acquire data from central regions of k-space during the predicted quiescent period and to acquire data for the peripheral regions of k-space elsewhere (e.g. in proximity to the predicted periodic events). Thus, scan and image artifacts can be reduced by such system.

Furthermore, the inventive system may comprise a validation unit capable of validating the MR data against real-time adaptive arrhythmia rejection criteria. The validation unit is capable of correlating the scan data and the physiological activity cycles. This is possible due to the real-time tracking of the physiology cycle durations in the inventive system. Consequently the cycle readings can be used to detect any (unpredicted) motions during data acquisition. As a result the scan data can either be used for image reconstruction if no physiological activity was detected during data acquisition or reacquired in the case that an arrhythmia occurred. Therefore, due to the validation procedure image artifacts may be further reduced.

It is further within the scope of the invention to disclose an adaptive steady-state free breathing MR imaging method, the method comprising the steps of:
 a) user input for the definition of at least one acquisition parameter of a steady-state MR sequence,
 b) monitoring physiological activity of a test subject,
 c) statistical analysis of the data monitored in step b),
 d) adjustment of at least one acquisition parameter of the MR sequence of step a), including adjustment of at least the starting points and/or the duration of RF-dummy excitations, according to the statistical analysis of step c),
 e) acquisition of MR scan of the test subject according to the parameter defined in step d),
 f) repetition of steps b) to e) until entire k-space is acquired.

Such method provides a prospective, adaptive, real-time method to overcome the existing limitations of breath-hold steady-state MR methods for both multi-phase and single-phase acquisitions in the context of for instance cardiac and respiratory gating. Therefore, such method is very suited in cases including test subjects with severely compromised breath holding capability and/or moderate arrhythmia, like sedated and uncooperative children, and adults. Especially such method may be very suited for steady state experiments, like a steady-state free precession (bSSFP) sequence, as already explained above. The proposed method will significantly diminish the burdens of the steady state constraint of uninterrupted periodic excitation for sequences such as bSSFP, and allow these sequences to be used with irregularly spaced interruptions in synchronization with physiologic signals. Therefore, the proposed method will additionally improve work-flow for the user in prescribing such singly or multiply interrupted steady state sequences such as SSFP, by providing the possibility of, for instance, seamless adaptation of k-space traversal and arrhythmia rejection criteria in real-time to minimize artefacts due to motion and approach to steady state. Finally, commercially available retrospective cardiac gating reconstruction algorithms may perform the required non-linear stretching of variable R-R intervals to reconstruct cine images.

The user input for the definition of the MR-sequence may be performed as known in the state of the art, e.g. by input of the necessary parameters using a user interface (Exam-Card), which inter alia allows the user to specify the maximum scan time (MST) to complete data acquisition. The overall method may be initiated in the validation phase of the protocol definition file (PDF) on the scanner console. If the prescribed protocol is using physiology synchronization and steady state MR sequence then PDF will compute the required time to steady state (TSS) using the time for repetition (TR), time to echo (TE) and flip angle (FA) of the prescribed sequence for scanner field strength. The PDF can either take the desired slice thickness for TSS from the user interface or use the look up table for prescribed physiologic phase for data acquisition. Along with standard measurement parameters PDF may pass TSS, TSS_slice_thickness, and MST to the measurement program file (MPF), which executes on the spectrometer.

In a preferred embodiment of the inventive method the statistical analysis in step c) at least includes the determination of the periodicity of the physiological activity. In order to predict the occurrences of physiological changes of a test subject it is very suitable to determine not only the occurrence, but to determine also the periodicity of the signals. This may be achieved by either simple calculation of the time difference between two triggers of a physiological cycle or by more sophisticated methods like a moving average of a number of trigger events or histogram analysis. Such more elaborated methods are preferred, because usually they allow an even better prediction, because they are based on a larger number of data points. Even more, such better statistical methods are also able to include nonlinear spacing between the trigger events. Suitable physiological triggers may be heart beat, respiration/expiration and/or blood flow.

According to the invention, in step d) at least the starting points and/or the duration of RF-dummy excitations are adjusted. For steady state MR sequences a defined set of RF excitations is usually used during which data acquisition is disabled (dummy excitations). These dummy excitations drive the magnetization toward steady state, after which data acquisition commences. In the case of physiological activity of a test subject it is therefore helpful to adjust, in addition to the data acquisition, also the starting points and/or the duration of the dummy excitations. This may help to keep the same steady state for different scans after an interruption occurred. Therefore, the same data quality for all the scans can be achieved.

In a preferred characteristic of the invention a method is disclosed, wherein in step d) at least the number of k-space segments is adjusted. Based on the statistical analysis of the physiological cycles of interest it is also advantageously possible to adjust the number and position of the k-space segments as a function of the statistical analysis. The central segments of the k-space may advantageously be filled in prospectively predicted quiet periods of the physiological cycles, wherein less central parts of the k-space can be filled using data, acquired near physiological events where motion of the test object may occur. A similar strategy may be used by adjusting the number of k-lines per shot. Thus a better image quality can be achieved. Such prospective evaluation of the correlation between data acquisition event and selected k-space segment may also be named k-space sampling strategy.

A preferred characteristic of the invention discloses a method, wherein the adjustment of the acquisition parameter in step d) is further based on the input of an RF-monitor. Besides the determination of periodic physiological trigger events it might also be helpful to additionally monitor the test subject by the use of a RF-monitor. Therefore, it is possible to additionally monitor non periodic movements of the test subject. Such monitor data may also form a basis for the statistical analysis or can additionally be used for instance in the course of a validation routine. Within this validation routine scans can be excluded, wherein large non-periodic motions of the test subject occurred. Thus, a better, artifact free image can be obtained.

In another embodiment of the invention it is also possible to use the prediction of an expiration phase and cardiac R-tops for the determination of the acquisition. For instance it is possible to use the first cardiac R-top as synchronization point for the acquisition of the segment of phase encoding steps in k-space in a multi-phase manner. This after steady state is attained and the expiration phase has started. On the arrival of the immediate $n^{th}$ (computed in real-time) R-top RF excitations will be terminated. The commercially available real-time arrhythmia rejection algorithm will either accept or reject the data at each heart beat. In case of rejection the same phase encoding segment will be reacquired.

An additional embodiment according to the invention comprises a method, wherein in an additional step the MR scan of step e) is validated against arrhythmia rejection criteria. In general it is also possible to use existing mechanisms and algorithms to track physiology signals and detect physiological activity. As an example, if data acquisition should proceed at the inspiratory point of respiratory signal, then the real-time arrhythmia rejection algorithm will also check if the inspiration phase has occurred during the data acquisition. The acquired scan data can be labeled according to the actual outcome of the tracked signal. For instance it is possible to label the scan "accepted", "rejected", or "marginal" based on the location in the k-space, in the cardiac cycle, and the extent of the inspiration. This includes an enhancement of the standard validation scale. Furthermore, the existing mechanism of labeling the acquired data to communicate with the reconstruction algorithm can be enhanced to allow 'marginal' label in addition to 'valid' and 'invalid' labels. Traversing the information rich center of k-space earlier in the acquisition will ensure that only marginal data is left before the MST is reached.

In a further preferred embodiment the free-breathing MR-pulse sequence is a respiratory triggered cardiac gated cine bSSFP sequence. In this case the inventive method can advantageously be used to obtain artifact free images. Within this method the user can prescribe the scan to trigger on inspiration or expiration with arrhythmia rejection, retrospective cardiac gating and number of heart beats to be used for acquisition per expiration phase. The inspiration trigger can be obtained from respiratory bellow and in the case of an expiration trigger it can be either from bellows or a RF navigator. RF navigator when used in track mode will allow motion compensation across the respiratory cycles.

Another characteristic of the inventive method may include the steps:

A. Prospectively calculate a histogram of the periodicity of each type of physiologic cycle in a patient and adaptively update the relational table of physiologic phase durations during the course of the MR examination.
B. Compute the duration of dummy RF excitations required to attain the steady state for the prescribed steady state MR pulse sequence (e.g. bSSFP) by taking the signal behavior of the pulse sequence, relaxation times of tissues of interest and the operator specified pulse sequence parameters such as TR/TE/flip angle into account.
C. Adaptively adjust the acquisition parameters based on patient specific physiologic or other constraints. For example, based on the user input for the maximum allowed time for acquisition, the type of gating and desired physiologic phase for gating, e.g. end-inspiration and retrospective cardiac and time required to attain steady state (from step B) determine the optimal time window available for preparation of steady state, slice thickness and/or slice profile of the steady state preparation, application of RF navigator and time window available for acquisition of data using table from step A.
D. Using the information from steps A to C the method will prospectively adapt the data acquisition in real-time:
  1. Acquire the RF navigator if deemed feasible in step C to assess the extent of the physiologic motion.
  2. Initiate the dummy RF excitations of predetermined slice thickness or profile at predetermined physiologic phase for steady state preparation determined in step C. If preceded by RF navigator the steady state preparation phase's slice position will be prospectively tailored to compensate for the motion and fresh spin effects.
  3. Initiate data acquisition at predetermined physiologic phase for data acquisition in step C after the application of dummy RF excitations for minimum time duration predetermined in step B.
  4. Adaptively adjust the number of k-space segments to maximize scan efficiency to completely fill the remaining time available with data acquisition for current physiologic cycle
  5. Use physiologic information obtained in step A to design a k-space sampling strategy that will minimize the likelihood of motion during the information-rich, central-portions of k-space e.g. prospectively plan to acquire data from central regions of k-space during the predicted quiescent period and peripheral regions of k-space elsewhere.
  6. Acquire the data in predetermined physiologic phase. If RF navigator is acquired then excitation for acquisitions will be adjusted to compensate for the motion.
  7. Upon completion of data acquisition validate the data against real-time adaptive arrhythmia rejection criteria based on physiologic phase during acquisition and relative position in the k-space. All acquired data will be stored in the database with labels based on the degree of user prescribed constraints to the algorithm, e.g., as excellent, acceptable, marginal, or unacceptable (and reacquire).
  8. Determine the next phase encoding steps based on the results of Step D(7) i.e. accept or reacquire the partial or complete data.
E. Repeat step D until entire k-space is acquired. If the predetermined maximum allocated time for the acquisition has elapsed stop the sequence or if time is still available reacquire data labeled as marginal to improve image quality further.

It is also within the scope of the invention to provide a computer program product, wherein the computer program product comprises computer executable instructions to perform the method steps according to the invention. Such computer program product may be used to implement the method using the standard hardware of commercial available MR machines.

In an additional embodiment of the invention the computer program product is an update program product. An update product within the meaning of the invention is a computer program product, which does not provide a full executable software code for running and controlling an MR-instrument, but is able to implement further features within the framework of the existing code. This might for instance be a statistical package or a modification of existing arrhythmia rejection routines.

With respect to additional advantages and features of the previously described system it is explicitly referred to the disclosure of the inventive method. In addition, also aspects and features of the inventive method shall be deemed applicable and disclosed to the inventive system and vice versa. Furthermore, all combinations of at least two features disclosed in the claims and/or in the description are within the scope of the invention unless otherwise explicitly indicated.

While the invention has been illustrated and described in detail in the description and the drawings such description and drawings is to be considered illustrative or exemplary and not restrictive. Other variations to the disclosed embodiments can be understood and effected by those skilled in the art in practicing the claimed invention, from a study of the disclosure, the drawings, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

BRIEF DESCRIPTION OF THE DRAWINGS

These and other aspects of the invention will be apparent from and elucidated with reference to the embodiments described hereinafter. Such embodiment does not necessarily represent the full scope of the invention, however, and reference is made therefore to the claims and herein for interpreting the scope of the invention. In the drawings:

FIG. 3 is a schematic illustration of a part of an embodiment to adaptively tailor k-space sampling strategy.

DETAILED DESCRIPTION OF EMBODIMENTS

Figure 1:
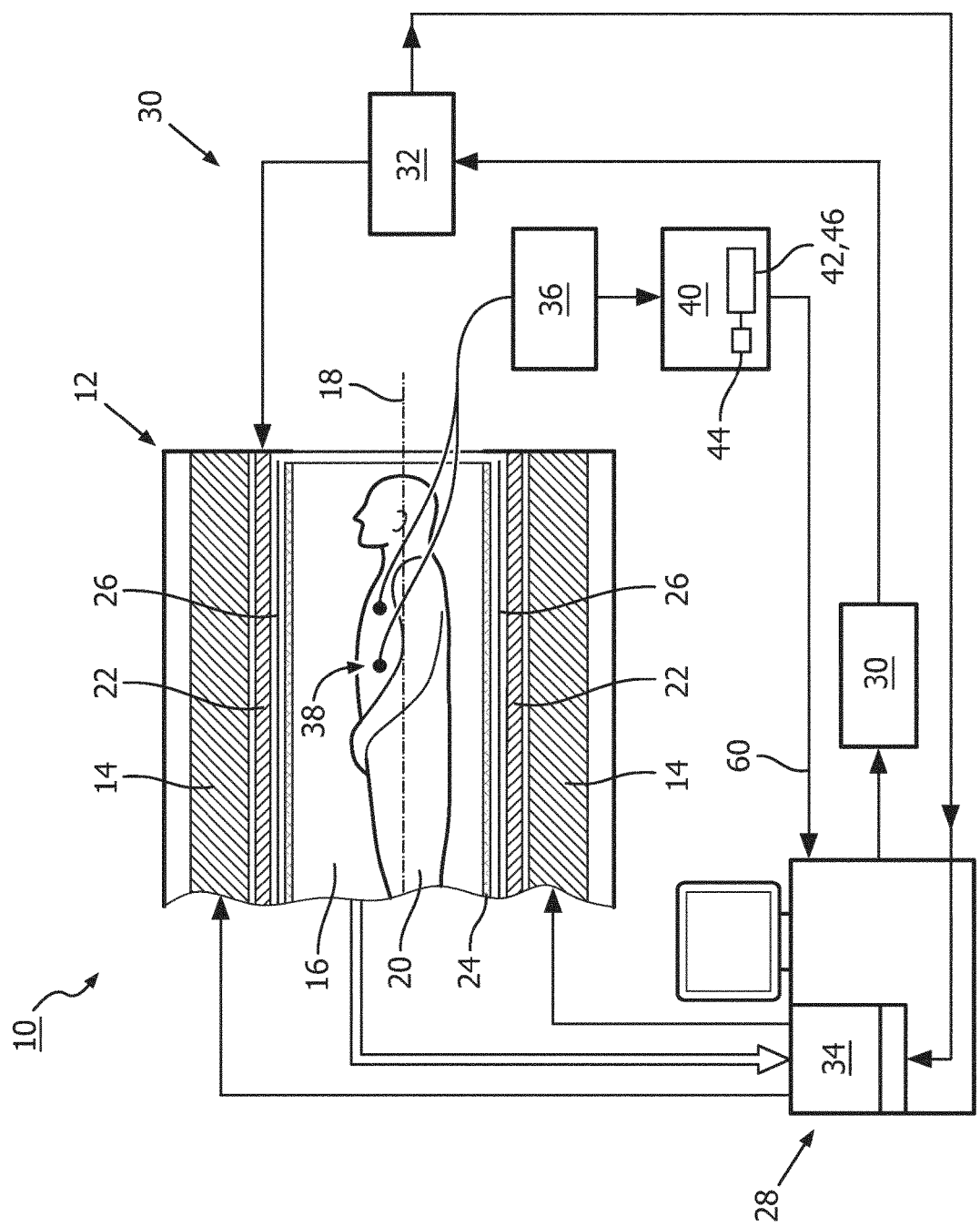
FIG. 1 is a schematic illustration of a part of an embodiment of a magnetic resonance imaging system in accordance with the invention.

FIG. 1 shows a schematic illustration of a part of an embodiment of a free-breathing Magnetic Resonance (MR) imaging system 10 in accordance with the invention, for acquisition of magnetic resonance images of a portion of a test subject 20. In particular, the magnetic resonance imaging system 10 is configured for acquisition of magnetic resonance images in a free-breathing experiment. The magnetic resonance imaging system 10 comprises a magnetic resonance scanner 12 having a main magnet 14 provided for generating a static magnetic field. The main magnet 14 has a central bore that provides an examination space 16 around a center axis 18 for the test subject 20, e.g. a human volunteer, to be positioned within. For clarity reasons, a conventional table for supporting the test subject 20 has been omitted in FIG. 1. The substantially static magnetic field defines an axial direction of the examination space 16, aligned in parallel to the center axis 18. Further, the magnetic resonance imaging system 10 includes a magnetic gradient coil system 22 provided for generating gradient magnetic fields superimposed to the static magnetic field. The magnetic gradient coil system 22 is concentrically arranged within the bore of the main magnet 14, as is known in the art.

Further, the magnetic resonance imaging system 10 comprises a radio frequency antenna 24 designed as a whole-body coil that is provided for applying a radio frequency magnetic field to the examination space 16 during radio frequency transmit phases to excite nuclei of the test subject 20. The radio frequency antenna 24 is also provided to receive magnetic resonance signals from the excited nuclei during radio frequency receive phases. In an operational state of the magnetic resonance imaging system 10, radio frequency transmit phases and radio frequency receive phases are taking place in a consecutive manner. The radio frequency antenna 24 has a center axis and, in the operational state, is arranged concentrically within the bore of the main magnet 14 such that the center axis of the radio frequency antenna 24 and the center axis 18 of the magnetic resonance imaging system 10 coincide. As is well known in the art, a cylindrical metal radio frequency screen 26 is arranged concentrically between the magnetic gradient coil system 22 and the radio frequency antenna 24. It is understood that all mentioned hardware parts responsible for signal and field generation and/or detection may be part of the magnetic field unit.

The free-breathing magnetic resonance imaging system 10 further includes a control unit 28 provided for controlling functions of the magnetic resonance scanner 12. Furthermore, the magnetic resonance imaging system 10 comprises a radio frequency transmitter unit 30 that is connected to and controlled by the control unit 28. The radio frequency transmitter unit 30 is provided to feed radio frequency power of a magnetic resonance radio frequency to the radio frequency antenna 24 via a radio frequency switching unit 32 during the radio frequency transmit phases. During radio frequency receive phases, the radio frequency switching unit 32 directs the magnetic resonance signals from the radio frequency antenna 24 to an image processing unit 34 residing in the control unit 28. The image processing unit 34 is configured for processing acquired magnetic resonance signals to determine a magnetic resonance image of the portion of the subject of interest 20 from the acquired magnetic resonance signals. Many different variations of this technique are well known to the person skilled in the art, and thus need not be described in further detail herein.

For the acquisition of magnetic resonance images of for instance the heart of the subject of interest 20, the magnetic resonance imaging system 10 may be further equipped with a detection unit 36 for detecting physiological activity of the test subject (e.g. an electrocardiogram device) and a data processing unit 40 capable of performing statistical analysis of the physiological activity data. The data processing unit 40 may also be a hardware part of the standard computer system of the MR-instrument.

The detection unit 36 is provided for taking measurements of the electrocardiogram data of the heart of the test subject 20 via a plurality of electrodes 38.

The detection unit 36 is coupled to the data processing unit 40, which is configured capable of performing statistical analysis of the physiological activity data and capable to adaptively tailor at least one of the parameters of the MR-pulse sequence based on the statistical analysis.

The parameter of the next and the following acquisition periods are determined by the data processing unit 40 based on a statistical analysis of the physiological activity data measured by detection unit 36. The data processing unit 40 is capable to adaptively tailor at least one of the parameters of the MR-pulse sequence based on the statistical analysis. The tailored parameter 60 is transmitted to the control unit 28. For this purpose, the data processing unit 40 may be furnished with a memory unit 42, a processor unit 44 and a software module 46, wherein steps of the adaptive steady-state free breathing MR imaging method are converted into a program code that is implemented in the memory unit 42 of the data processing unit 40 and that is executable by the processor unit 44 of the data processing unit 40. Furthermore, it is also possible that the data processing unit is fully implemented into the hardware part of the standard MR-computer system.

Figure 2:
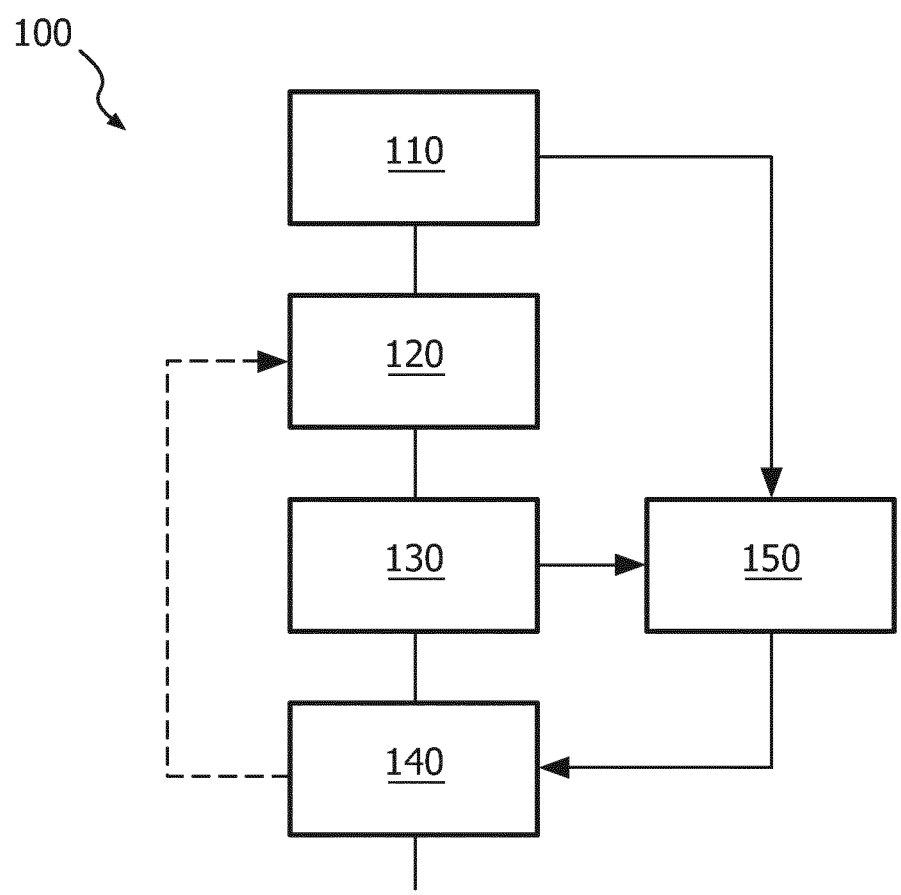
FIG. 2 is a schematic illustration of a part of an embodiment of the inventive method.

FIG. 2 shows a schematic illustration of the steps of the inventive adaptive steady-state free breathing MR imaging method 100. In step 110 a user may define one or several acquisition parameter of a steady-state MR sequence. These parameters may be stored in a parameter table 150. In a second step 120, the physiological activity of a test subject is monitored over time. Suitable monitoring parameter may be respiration or heart beat. According to the acquired parameter a statistical analysis is performed in 130 based on the physiological activity data monitored in 120. Here, especially the periodicities of the physiological cycle(s) may be determined. According to the statistical analysis of 130 the acquisition parameter stored in the parameter table 150 are adjusted, for instance by adapting RF-excitation starting time and/or k-space sampling strategy. Steps 120, 130, 150, 140 may be repeated until the entire k-space is acquired.

FIG. 3 shows a schematic illustration of the result of the adaption of the k-space sampling strategy. The k-space sampling is prospectively adapted in a way that the central parts of the k-space are sampled during quite periods, where no motion of the test subject is expected. Data sampled near an expected motion of a subject may either be omitted or be used to fill the non-central parts of the k-space.

REFERENCE SYMBOL LIST

10 magnetic resonance imaging system
12 magnetic resonance scanner
14 main magnet
16 examination space
18 center axis
20 Test subject
22 magnetic gradient coil system
24 radio frequency antenna
26 radio frequency screen
28 control unit
30 radio frequency transmitter unit
32 radio frequency switching unit
34 image processing unit
36 detection unit
38 Electrode
40 data processing unit
42 memory unit
44 processor unit
46 software module
60 adaptively tailored data
100 method
110 user Input
120 monitoring
130 statistical Analysis and Tailoring
140 acquisition
150 parameters defining a MR-pulse sequence

The invention claimed is:

1. A Magnetic Resonance (MR) imaging system for generating an MR image of a test subject, the MR imaging system at least comprising:
   a control unit for controlling functions of the MR imaging system;
   a user interface adapted to receive parameters defining a MR-pulse sequence;
   a detection unit for detecting physiological activity of the test subject; and
   a data processing unit adapted to perform statistical analysis of physiological activity data and configured to adaptively tailor the parameters of the MR-pulse sequence based on the statistical analysis, wherein the parameters of the MR-pulse sequence include adjustment of at least starting points and duration of RF-dummy excitations, which are part of the MR-pulse sequence.

2. The MR system according to claim 1, further comprising a magnetic field unit and an image processing unit operably coupled to the control unit.

3. The MR system according to claim 1, wherein the statistical analysis of the physiological activity data comprises at least one selected from a determination of periodicity of a respiratory and a cardiac cycle of a test subject.

4. The MR system according to claim 1, wherein the MR-pulse sequence is a balanced steady state free precession sequence.

5. The MR system according to claim 1, wherein the data processing unit is adapted to tailor RF-excitation and/or a start of data acquisition.

6. The MR system according to claim 1, wherein the data processing unit is adapted to tailor k-space sampling.

7. The MR system according to claim 1, wherein the system further comprises a validation unit adapted to MR data against real-time adaptive arrhythmia rejection criteria.

8. An adaptive steady-state free breathing magnetic resonance (MR) imaging method, the method comprising the steps of:
   a) receiving user input for a definition of at least one acquisition parameter of a steady-state MR sequence,
   b) monitoring physiological activity of a test subject,
   c) analyzing data monitored in step b), wherein analyzing includes a statistical analysis of the data monitored,
   d) adjusting at least one acquisition parameter of the steady-state MR sequence of step a), including adjustment of at least starting points and/or duration of RF-dummy excitations, according to the statistical analysis of step c, wherein the adjustment of the acquisition parameter is based on an input of an RF-monitor,
   e) acquiring the MR scan of the test subject according to the parameter defined in step d), and
   f) repeating steps b) to e) until an entire k-space is acquired.

9. The method according to claim 8, wherein the statistical analysis in step c) at least includes determination of a periodicity of the physiological activity.

10. The method according to claim 8, wherein step d) at least a number of k-space segments is adjusted.

11. The method according to claim 8, wherein in an additional step the MR scan of step e) is validated against arrhythmia rejection criteria.

12. A non-transitory computer-readable medium, comprising instructions, which when executed on a computer cause the computer to perform the method steps as claimed in claim 8.

13. The non-transitory computer-readable medium according to claim 12, wherein the instructions are an update program product.

14. The MR system according to claim 1, wherein the at least one of the parameters of the MR-pulse sequence are a function of tissue of interest.

15. The MR system according to claim 1, wherein the at least one of the parameters of the MR-pulse sequence are maximum scan time (MST), time to steady state (TSS), time for repetition (TR), time to echo (TE) and flip angle (FA).

16. The MR system according to claim 1, wherein an MR signal is prospectively gated to acquire also in conjunction with a respiratory signal.

17. The MR system according to claim 16, wherein an MR signal acquisition process is interrupted with a trigger, which has a regularity is governed by respiration or cardiac pulsation.

18. The MR system according to claim 4, wherein the balanced steady state free precession sequence is used with irregularly spaced interruptions in synchronization with physiologic signals.

19. The MR system according to claim 7, wherein validation unit is configured to correlate scan data and physiological activity cycles.

20. The method according to claim 9, wherein the physiological activity comprises respiratory activity, or a cardiac cycle, or both.

* * * * *